(12) United States Patent
Casey (10) Patent No.: US 7,351,261 B2
(45) Date of Patent: Apr. 1, 2008

(54) MULTI-JOINT IMPLANT

(75) Inventor: Niall Casey, Boston, MA (US)

(73) Assignee: DePuy Spine, Inc., Raynham, MA (US)

(*) Notice: Subject to any disclaimer, the term of this patent is extended or adjusted under 35 U.S.C. 154(b) by 276 days.

(21) Appl. No.: 10/908,787

(22) Filed: May 26, 2005

(65) Prior Publication Data

US 2006/0004448 A1 Jan. 5, 2006

Related U.S. Application Data

(60) Provisional application No. 60/584,022, filed on Jun. 30, 2004.

(51) Int. Cl.
*A61F 2/44* (2006.01)

(52) U.S. Cl. .................. 623/17.13; 623/17.15

(58) Field of Classification Search .. 623/17.11–17.16; 606/61
See application file for complete search history.

(56) References Cited

U.S. PATENT DOCUMENTS

| | | | |
|---|---|---|---|
| 4,743,260 A | 5/1988 | Burton | |
| 5,092,866 A | 3/1992 | Breard et al. | |
| 5,282,863 A | 2/1994 | Burton | |
| 5,387,213 A | 2/1995 | Breard et al. | |
| 5,415,661 A | 5/1995 | Holmes | |
| 5,474,086 A | 12/1995 | McCormick et al. | |
| 5,540,688 A | 7/1996 | Navas | |
| 5,556,431 A | 9/1996 | Buttner-Janz | |
| 5,562,737 A | 10/1996 | Graf | |
| 5,571,191 A | 11/1996 | Fitz | |
| 5,672,175 A | 9/1997 | Martin | |
| RE36,221 E | 6/1999 | Breard et al. | |
| 5,961,516 A | 10/1999 | Graf | |
| RE36,758 E | 6/2000 | Fitz | |
| 6,132,464 A | 10/2000 | Martin | |
| 6,267,764 B1 | 7/2001 | Elberg | |
| 6,273,888 B1 | 8/2001 | Justis | |
| 6,419,703 B1 | 7/2002 | Fallin et al. | |
| 6,554,831 B1 | 4/2003 | Rivard et al. | |
| 6,565,605 B2 | 5/2003 | Goble et al. | |
| 6,579,319 B2 | 6/2003 | Goble et al. | |
| 6,610,091 B1 | 8/2003 | Reiley | |
| 6,645,207 B2 | 11/2003 | Dixon et al. | |
| 6,669,729 B2 | 12/2003 | Chin | |
| 6,811,567 B2 | 11/2004 | Reiley | |
| 2002/0065557 A1 | 5/2002 | Goble et al. | |

(Continued)

FOREIGN PATENT DOCUMENTS

EP 0669109 2/1994

(Continued)

*Primary Examiner*—Bruce Snow
(74) *Attorney, Agent, or Firm*—Nutter, McClennen & Fish, LLP (57) ABSTRACT

Methods and devices are provided for repairing or replacing damaged, injured, diseased, or otherwise unhealthy posterior elements, such as the facet joints, the lamina, the posterior ligaments, and/or other features of a patient's spinal column. In one exemplary embodiment, an implant is provided having an anterior portion that is adapted to be positioned between adjacent vertebrae and a posterior portion that is adapted to be positioned around a spinal cord and to couple to a posterior surface of at least one adjacent vertebra. In use, the implant can allow the adjacent vertebrae to move relative to one another, thereby restoring normal function to the vertebrae.

5 Claims, 5 Drawing Sheets

U.S. PATENT DOCUMENTS

| | | |
|---|---|---|
| 2002/0072800 A1 | 6/2002 | Goble et al. |
| 2002/0123806 A1 | 9/2002 | Reiley |
| 2002/0133155 A1 | 9/2002 | Ferree |
| 2003/0004572 A1 | 1/2003 | Goble et al. |
| 2003/0028250 A1 | 2/2003 | Reiley et al. |
| 2003/0055427 A1 | 3/2003 | Graf |
| 2003/0083657 A1 | 5/2003 | Drewry |
| 2003/0109880 A1 | 6/2003 | Shirado et al. |
| 2003/0135277 A1 | 7/2003 | Bryan et al. |
| 2003/0153912 A1 | 8/2003 | Graf |
| 2003/0171749 A1 | 9/2003 | Le Couedic et al. |
| 2003/0171750 A1 | 9/2003 | Chin |
| 2003/0191470 A1 | 10/2003 | Ritland |
| 2003/0191532 A1 | 10/2003 | Goble et al. |
| 2003/0220642 A1 | 11/2003 | Freudiger |
| 2003/0220643 A1 | 11/2003 | Ferree |
| 2004/0002708 A1 | 1/2004 | Ritland |
| 2004/0006391 A1 | 1/2004 | Reiley |
| 2004/0049189 A1 | 3/2004 | Le Couedic et al. |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0073215 A1 | 4/2004 | Carli |
| 2004/0111154 A1 | 6/2004 | Reiley |
| 2004/0116927 A1 | 6/2004 | Graf |
| 2004/0143264 A1 | 7/2004 | McAfee |
| 2004/0186475 A1 | 9/2004 | Falahee |
| 2004/0236329 A1 | 11/2004 | Panjabi |
| 2005/0033431 A1 | 2/2005 | Gordon et al. |
| 2005/0033432 A1 | 2/2005 | Gordon et al. |
| 2005/0033439 A1 | 2/2005 | Gordon et al. |
| 2005/0101954 A1 | 5/2005 | Simonson |
| 2005/0101956 A1 | 5/2005 | Slmonson |
| 2005/0113927 A1 | 5/2005 | Malek |
| 2005/0171609 A1* | 8/2005 | Humphreys et al. ..... 623/17.15 |

FOREIGN PATENT DOCUMENTS

| | | |
|---|---|---|
| WO | WO-01/45576 | 6/2001 |
| WO | WO-02/17803 | 3/2002 |
| WO | WO-02/43603 | 6/2002 |
| WO | WO-02/102259 | 12/2002 |
| WO | WO-03/007828 | 1/2003 |
| WO | WO-03/009737 | 2/2003 |
| WO | WO-2004/024011 | 3/2004 |
| WO | WO-2004/034916 | 4/2004 |

* cited by examiner

MULTI-JOINT IMPLANT

CROSS REFERENCE TO RELATED APPLICATIONS

The present invention claims priority to U.S. Provisional Application Ser. No. 60/584,022, filed on Jun. 30, 2004 and entitled "Multi-Joint (Disc & Facet) Implant," which is hereby incorporated by reference in its entirety.

FIELD OF THE INVENTION

The present invention relates to spinal implants and methods.

BACKGROUND OF THE INVENTION

The vertebrae in a patient's spinal column are linked to one another by the disc and the facet joints, which control movement of the vertebrae. Each vertebra has a pair of articulating surfaces located on the left side, and a pair of articulating surfaces located on the right side, and each pair includes a superior articular surface, which faces upward, and an inferior articular surface, which faces downward. Together the superior and inferior articular surfaces of adjacent vertebra form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another. In combination with the intervertebral disc, the two facet joints form the spinal three-joint complex.

Diseased, degenerated, impaired, or otherwise painful facet joints and/or discs can require surgery to relieve pain or restore function to the three-joint complex. Subsequent surgery may also be required after a laminectomy, as a laminectomy predisposes the patient to instability and may lead to post-laminectomy kyphosis (abnormal forward curvature of the spine), pain, and neurological dysfunction. Current clinical data have suggested that degeneration of one member of the three joint complex, that is either the discs or the facet joints, contributes to the degeneration of the other. While implants are available for replacing either a diseased disc or the facet joints, there are no implants that can be used to replace the entire spinal three-joint complex.

Accordingly, there remains a need for improved systems and methods for repairing and/or replacing the spinal three-joint complex.

BRIEF SUMMARY OF THE INVENTION

The present invention provides various methods and devices for repairing or replacing damaged, injured, diseased, or otherwise unhealthy posterior elements, such as the facet joints, the lamina, the posterior ligaments, and/or other features of a patient's spinal column. In one exemplary embodiment, a spinal implant is provided having an anterior portion that is adapted to be positioned between adjacent vertebrae, and a posterior portion that is adapted to be positioned around a spinal cord and to couple to at least one adjacent vertebra.

The implant can have a variety of shapes and sizes, but in one exemplary embodiment the implant is substantially C-shaped such that the posterior portion is curved or semi-circular with an opening formed therein and the anterior portion includes opposed arms that extend from the posterior portion. The posterior and anterior portions of the implant can have a variety of configurations, but in one exemplary embodiment the anterior portion of the implant has a shape that is adapted to allow articulation of adjacent vertebrae relative to one another, and the posterior portion of the implant includes at least one extension member extending therefrom and adapted to mate to a posterior surface of a vertebra. The extension member(s) can have a variety of configurations, and it can be rigidly or movably coupled to the implant. In one exemplary embodiment, the extension member(s) is an elongate member having at least one thru-bore formed therein for receiving a fastening element adapted to mate the extension member(s) to a vertebra. The implant can also include any number of extension members, but in one exemplary embodiment the implant includes first and second extension members extending from opposed lateral sides of the posterior portion of the implant. The first and second extension members can extend in a superior direction from a superior surface of the posterior portion of the C-shaped member, or alternatively they can extend in an inferior direction from an inferior surface of the posterior portion of the implant. In another exemplary embodiment, the implant can include first and second superior extension members extending in a superior direction from opposed lateral sides of the posterior portion of the implant, and first and second inferior extension members extending in an inferior direction from opposed lateral sides of the posterior portion of the implant.

In another exemplary embodiment, the implant can include a substantially C-shaped superior member, a substantially C-shaped inferior member, and at least one central member disposed therebetween. In certain embodiments, the implant can include first and second central members disposed between the anterior portion of the superior and inferior members, and third and fourth central members disposed between the posterior portion of the superior and inferior members. In use, the central member(s) can be adapted to articulate between the superior and inferior members. In other embodiments, the central member(s) can be compressible to allow movement of the superior and inferior members relative to one another.

The present invention also provides exemplary methods for stabilizing adjacent vertebrae. In one embodiment, the method can include positioning a posterior portion of an implant around a spinal cord and between resected facets of adjacent vertebrae. The posterior portion of the implant can be adapted to couple to at least one of the adjacent vertebrae. The method can further include positioning an anterior portion of the implant between the adjacent vertebrae such that the adjacent vertebrae are adapted to move relative to one another.

In another exemplary embodiment, a method for stabilizing adjacent vertebrae is provided and includes accessing a patient's spinal column using a posterior surgical approach, removing a disc disposed between adjacent vertebrae, posteriorly positioning an implant around a spinal cord, between facet joints of adjacent vertebrae, and between the adjacent vertebrae, and coupling a posterior portion of the implant to at least one of the adjacent vertebrae. In an exemplary embodiment, the posterior portion of the implant is coupled to at least one of the adjacent vertebrae by inserting at least one bone screw through at least one extension formed on the posterior portion of the implant and into the vertebra.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides various methods and devices for repairing or replacing damaged, injured, diseased, or otherwise unhealthy posterior elements, such as the facet joints, the lamina, the posterior ligaments, and/or other features of a patient's spinal column. In one exemplary embodiment, an implant is provided having an anterior portion that is adapted to be positioned between adjacent vertebrae and a posterior portion that is adapted to be positioned around a spinal cord and to couple to at least one adjacent vertebra. In use, the implant can allow the adjacent vertebrae to move relative to one another, thereby restoring normal function to the vertebrae.

Figure 1A:
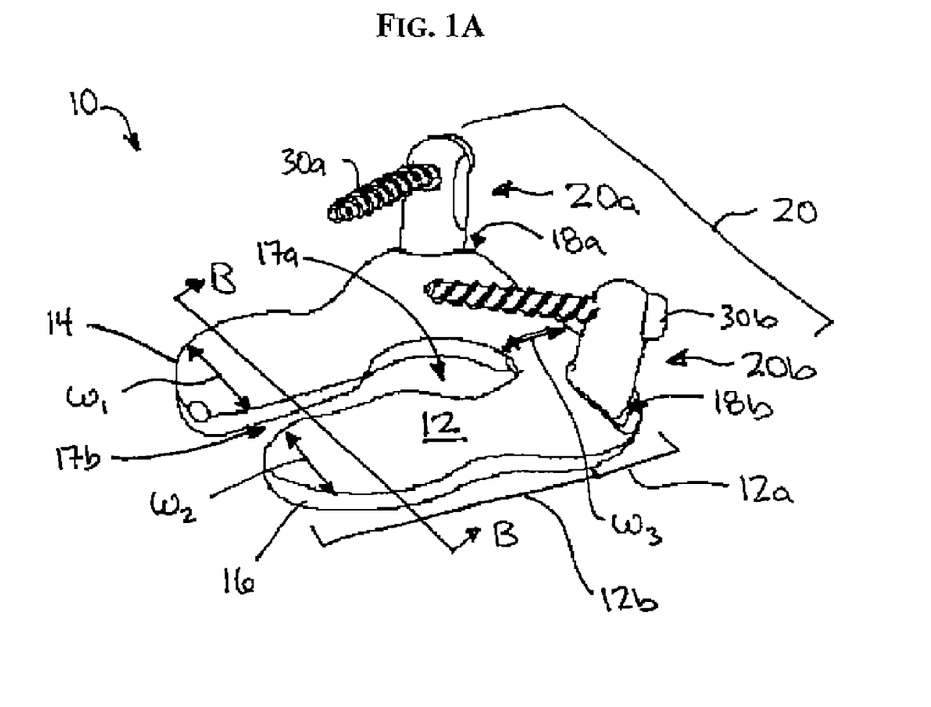
FIG. 1A is a perspective view of one exemplary embodiment of a spinal implant having a unitary disc replacement member with first and second facet replacement members movably coupled thereto.
Figure 1B:
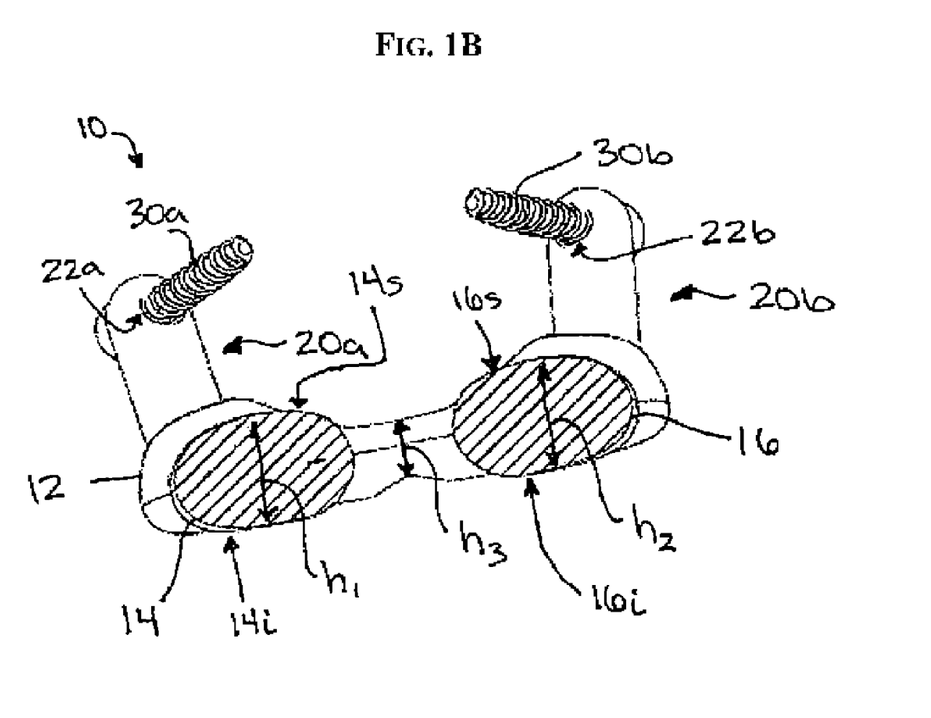
FIG. 1B is a cross-sectional view of the spinal implant shown in FIG. 1A taken across line B-B.

FIGS. 1A-1B illustrate one exemplary embodiment of a spinal implant 10 for replacing or repairing a damaged spinal disc, the facet joints, and optionally other posterior elements of the spine. In general, the implant 10 includes a posterior portion 12a that is adapted to be positioned around the spinal cord, and an anterior portion 12b that is adapted to be positioned between adjacent vertebrae. The anterior and posterior portions 12a, 12b are collectively referred to herein as a disc replacement component 12. The implant 10 can also include a facet replacement component 20 that is adapted to couple the disc replacement component 12 to at least one adjacent vertebrae. In use, the facet replacement component 20 can move relative to the disc replacement component 12 to allow the adjacent vertebrae to move relative to one another, thereby restoring normal function to the vertebrae.

The disc replacement component 12 can have a variety of configurations, but in the illustrated exemplary embodiment it is substantially U-shaped or C-shaped. A person skilled in the art will appreciate that the terms "U-shaped" or "C-shaped" are intended to include any implant having a generally or partially curved structure with an opening in one side thereof. Further, these terms are intended to include any implant that has an open anterior portion and a posterior portion that can be disposed around a spinal cord, and an anterior portion that can be disposed between adjacent vertebrae. The shape and configuration of the implant is not intended to be limited to only a U- or C-shaped configuration.

The posterior portion 12a of the disc replacement component 12 can have a variety of shapes and sizes, but in the illustrated exemplary embodiment the posterior portion 12a is in the form of a substantially semi-circular member having a relatively large central opening 17a formed therein. Such a shape allows the posterior portion 12a to be positioned around the spinal cord in a patient's spinal column. The posterior portion 12a can also have a relatively low profile, so as to allow the posterior portion 12a to be positioned between the spinous processes of adjacent vertebrae.

The anterior portion 12b of the disc replacement component 12 can also have a variety of shapes and sizes, but in the illustrated exemplary embodiment the anterior portion 12b of the disc replacement component 12 includes opposed arms 14, 16 that extend from the posterior portion 12a in a substantially parallel arrangement and that define an opening 17b therebetween. The opening 17b between the arms 14, 16 can be smaller than the opening 17a at the posterior portion 12a of the disc replacement component 12, but it is preferably large enough to allow the spinal cord to pass therethrough when the implant 10 is being implanted. While the shape and size of each arm 14, 16 can vary, in one exemplary embodiment each arm 14, 16 is in the form of a lobe that extends from the posterior portion 12a, and that has a height $h_1$, $h_2$ that is greater than a height $h_3$ of the posterior portion 12a, and a width $w_1$, $w_2$ that is greater than a width $w_3$ of the posterior portion 12a of the implant 10, as shown in FIGS. 1A and 1B. Such a configuration allows the arms 14, 16 to occupy additional space between the adjacent vertebrae, thereby providing sufficient support for the vertebrae.

The opposed arms 14, 16 can also include a variety of other features that can vary depending on the intended use and desired result once implanted. For example, in one exemplary embodiment each arm 14, 16 can have a shape that is adapted to allow the adjacent vertebrae to articulate relative thereto. For example, as shown in FIGS. 1A and 1B, each arm 14, 16 includes curved or domed superior and inferior surfaces 14s, 16s, 14i, 16i. The domed surfaces 14s, 16s, 14i, 16i can be formed on any portion of each arm 14, 16, but in one exemplary embodiment the domed surfaces 14s, 16s, 14i, 16i are formed along the anterior portion 12b of the implant 10 adjacent to the terminal end of each arm 14, 16. As a result, when the arms 14, 16 are positioned between adjacent vertebrae, the domed surfaces 14s, 16s, 14i, 16i will be substantially centrally located relative to the adjacent vertebrae, thereby allowing the vertebrae to articulate relative thereto. While domed surfaces 14s, 16s, 14i, 16i are shown, the arms 14, 16 can have a variety of other configurations to allow articulation of adjacent vertebrae. For example, each arm 14, 16 can include a ball or other member movably disposed therein or coupled thereto.

In another exemplary embodiment, the opposed arms 14, 16 can be adapted to engage the adjacent vertebrae. Techniques for mating the arms 14, 16 to adjacent vertebrae include, by way of non-limiting example, surface features, such as teeth, that engage the endplates of the vertebrae, surface coatings or materials that allow bone growth into the implant 10 to occur, or other materials or features that will engage the adjacent vertebrae.

In an exemplary embodiment, where engagement features are included, at least a portion of the implant 10 is preferably compressible to allow movement between the adjacent vertebrae. For example, the arms 14, 16, or a portion of the arms 14, 16, can be compressible by forming the arms 14, 16 from a compressible material, embedding a compressible material in the arms 14, 16, or by coupling a compressible material to a portion of the arms 14, 16. Suitable compressible materials include, by way of non-limiting example, biocompatible polymers and metals.

As previously indicated above, the implant 10 can also include a facet replacement component 20 that is adapted to couple the disc replacement component 12 to at least one adjacent vertebrae. While the facet replacement component 20 can have a variety of configurations, and it can be formed integrally with, coupled to, or be separate from the disc replacement component 12, in one exemplary embodiment, as shown in FIGS. 1A and 1B, the facet replacement component 20 is in the form of first and second lateral extensions 20a, 20b that extend from the disc replacement component 12. The lateral extensions 20a, 20b are coupled to opposed sides of the posterior portion 12a of the disc replacement component 12, and they can extend in either a superior direction, as shown, to couple to a superior vertebra, or they can extend in an inferior direction. A person skilled in the art will appreciate that the implant 10 can include any number of lateral extensions extending in any direction to facilitate attachment thereof to one or more vertebrae.

Each extension 20a, 20b can be coupled to the disc replacement member 12 using a variety of techniques. In one exemplary embodiment, as shown, the extensions 20a, 20b are movably coupled to the disc replacement member 12 to allow the extensions 20a, 20b to pivot with respect to the disc replacement member 12 as the adjacent vertebrae move. A movable connection can be formed using, for example, a ball and socket joint, a polyaxial joint, flexible extensions 20a, 20b, etc. Alternatively, the extensions 20a, 20b do not need to be connected to the disc replacement member 12, but rather they can merely be disposed within corresponding recesses or sockets formed within the disc replacement member 12, as shown in FIG. 1A which illustrates first and second recesses 18a, 18b formed in the posterior portion 12a of the disc replacement member 12. While not necessary, an interference fit, a compression fit, or a mechanical interlock can optionally be used to retain the extensions 20a, 20b within the recesses 18a, 18b. A person skilled in the art will appreciate that a variety of techniques can be used to provide a movable connection between the facet replacement member 20 and the disc replacement member 12.

Each extension 20a, 20b can also have a variety of shapes and sizes, and the particular shape and size can vary depending on the intended implant location. In the illustrated embodiment, each extension 20a, 20b has a substantially elongate cylindrical shape with rounded or spherical ends. One of the spherical ends on each extension 20a, 20b allows the extension 20a, 20b to pivot within the recesses 18a, 18b formed in the disc replacement member 12. The other end of each extension 20a, 20b is preferably spherical to avoid potential damage to surrounding tissue. The size of each extension 20a, 20b can also vary, but in an exemplary embodiment each extension 20a, 20b preferably has a length that allows the extensions 20a, 20b to mate to the pedicles or lamina of a vertebra.

The extensions 20a, 20b can also include features to facilitate attachment to a vertebra. While virtually any technique can be used, including both rigid and dynamic connections, in one exemplary embodiment each extension 20a, 20b can be adapted to receive a fastening element for mating the extensions 20a, 20b to a vertebra. As shown in FIGS. 1A and 1B, each extension 20a, 20b includes a thru-bore 22a, 22b formed therein with a bone screw 30a, 30b disposed therethrough. The bone screws 30a, 30b can be polyaxially movable relative to the thru-bores 22a, 22b of the extensions 20a, 20b, but in an exemplary embodiment the bone screws 30a, 30b are monoaxial to rigidly connect the extensions 20a, 20b to a vertebra.

Figure 1C:
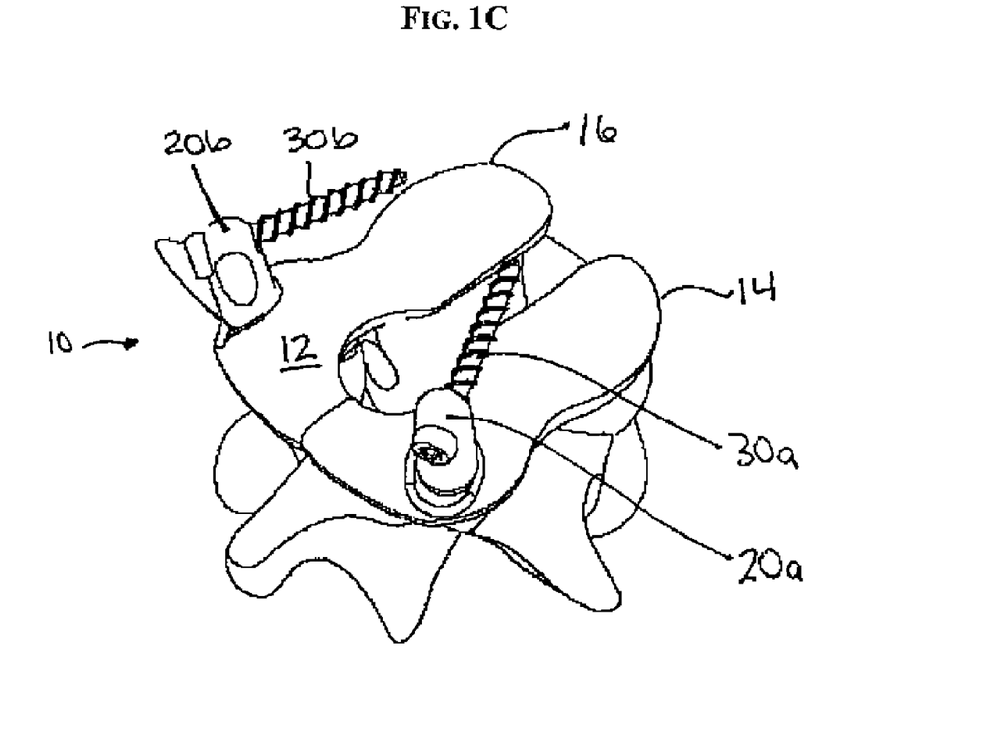
FIG. 1C is a superior perspective view of the spinal implant shown in FIG. 1A implanted between adjacent vertebrae, showing only the inferior vertebra.
Figure 1D:
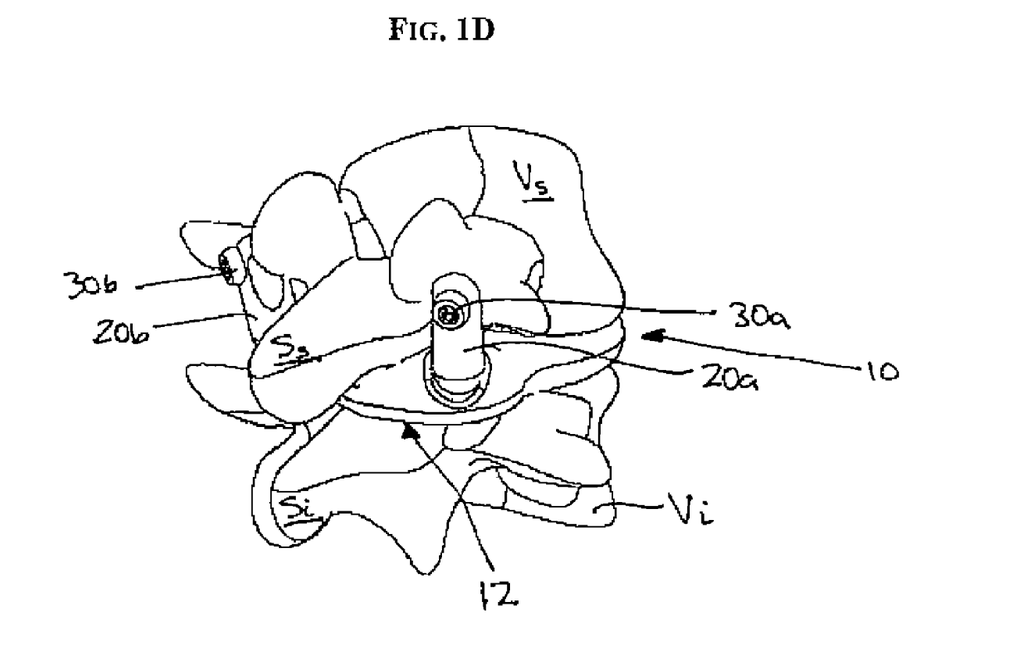
FIG. 1D is a posterior perspective view of the spinal implant shown in FIG. 1A implanted between adjacent superior and inferior vertebrae.

FIGS. 1C and 1D illustrate the implant 10 in use positioned between adjacent superior and inferior vertebrae $V_s$, $V_i$ (FIG. 1C only illustrates the inferior vertebra $V_i$). In an exemplary embodiment, the spinal column is accessed using a posterior surgical approach (which can include posteriolateral approaches). Minimally invasive techniques can be used to access the spinal column. Once the spinal column is accessed, and prior to positioning the implant 10 between adjacent superior and inferior vertebrae $V_s$, $V_i$, standard surgical techniques can be used to remove the natural disc disposed between the adjacent vertebrae $V_s$, $V_i$, and also the facet joints extending between the adjacent vertebrae $V_s$, $V_i$.

Once the disc and/or facets are prepared, the implant 10 can be guided between the adjacent vertebrae $V_s$, $V_i$ by passing the spinal cord through the opening 17b between the opposed arms 14, 16 of the disc replacement member 12, and into the opening 17c in the posterior portion 12a of the disc replacement member 12. A spinal distractor or other devices known in the art can be used to distract the adjacent vertebrae $V_s$, $V_i$ and guide the disc replacement member 12 therebetween. Alternatively, the disc replacement member 12 can have a shape that is adapted to distract the vertebrae $V_s$, $V_i$ as the disc replacement member 12 is inserted therebetween. Once implanted, as shown, the opposed arms 14, 16 are positioned between the adjacent vertebrae $V_s$, $V_i$, and the posterior portion 12a of the implant is positioned around the spinal cord and between the spinous processes $S_s$, $S_i$ of the adjacent vertebrae $V_s$, $V_i$. The adjacent vertebrae $V_s$, $V_i$ can articulate relative to the disc replacement member 12, or alternatively the disc replacement member 12 can be adapted to engage the adjacent vertebrae $V_s$, $V_i$, as previously discussed.

Once the disc replacement member 12 is properly positioned, the extension members 20a, 20b can be positioned within the recesses 18a, 18b in the disc replacement member 12, or can otherwise be coupled to the disc replacement member 12. A fastening element can be inserted through each extension member 20a, 20b and into the pedicles or lamina of the vertebra to couple the extension member 20a, 20b to the vertebra. As shown in FIG. 1D, first and second bone screws 30a, 30b are inserted through the extension members 20a, 20b and into the pedicles of the superior vertebra $V_s$ (or the pedicles of an inferior vertebra $V_i$, if desired). While the extension members 20a, 20b are rigidly connected to the superior vertebra $V_s$, the extension members 20a, 20b can move with respect to the disc replacement member 12, thereby allowing the adjacent vertebrae $V_s$, $V_i$ to articulate relative to one another.

Figure 2A:
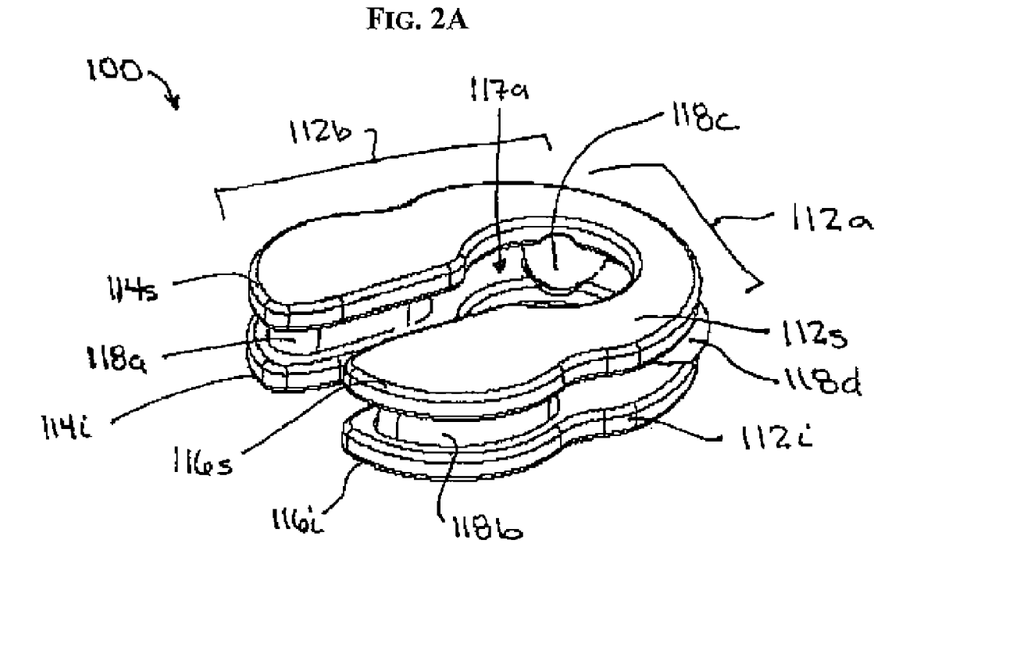
FIG. 2A is an anterior perspective view of another exemplary embodiment of a spinal implant having a multi-piece construction.
Figure 2B:
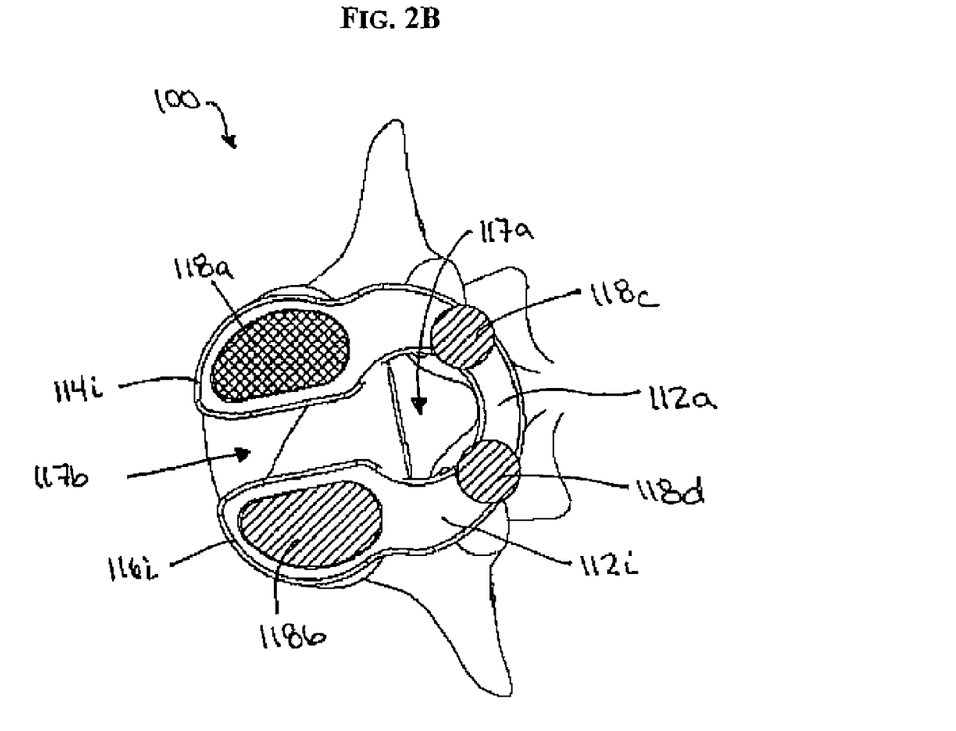
FIG. 2B is a superior cross-sectional view, taken in the axial plane, of the spinal implant shown in FIG. 2A implanted between adjacent vertebrae, showing only the inferior vertebra.

FIGS. 2A and 2B illustrate another exemplary embodiment of a spinal implant 100. The implant 100 is similar to implant 10 and generally includes a posterior portion 112a that is adapted to be positioned around a spinal cord and that can be coupled to at least one adjacent vertebrae, and an anterior portion 112b that is adapted to be positioned between adjacent vertebrae. In this embodiment, however, the implant 100 does not have a unitary configuration, but rather it has a multi-piece construction. In particular, the implant 100 includes a superior member 112s, an inferior member 112i, and at least one central member disposed therebetween and adapted to allow movement of the superior and inferior members 112s, 112i relative to one another.

The superior and inferior members 112s, 112i can vary in shape and size, but in one exemplary embodiment the superior and inferior members 112s, 112i are substantially U- or C-shaped such that that posterior portion 112a of the implant 100 is substantially curved or semi-circular with a central opening 117a formed therein to allow the implant 100 to be positioned around the spinal cord using a posterior surgical approach, and the anterior portion 112b of the implant 100 includes opposed superior and inferior arms 114s, 116s, 114i, 116i that can be positioned between adjacent vertebrae and that define an opening 117b therebetween for allowing the spinal cord to pass therethrough. The superior and inferior members 112s, 112i can also have substantially planar configurations, or they can have a shape that is adapted to match the contour of a vertebral endplate.

As indicated above, the implant 100 can also include at least one central member disposed between and adapted to allow movement of the superior and inferior members 112s, 112i relative to one another. While the implant 100 can include any number of central members, in the illustrated exemplary embodiment the implant 100 includes a four central members 118a, 118b, 118c, 118d disposed between the superior and inferior members 112s, 112i. In particular, a first central member 118a is positioned between the first superior arm 114s and the first inferior arm 114i, a second central member 118b is positioned between the second superior arm 114s and the second inferior arm 114i, and third and fourth central members 118c, 118d are positioned on opposed lateral sides of the posterior portion 112a of the implant 100 between the superior and inferior members 112s, 112i.

The central members 118a, 118b, 118c, 118d can be coupled to the superior and inferior members 112s, 112i, or they can be removably disposed between the superior and inferior members 112s, 112i. For example, in one embodiment the central members 118a, 118b, 118c, 118d can be fixedly mated to one or both of the superior and inferior members 112s, 112i. The central members 118a, 118b, 118c, 118d can, however, be adapted to pivot, rotate, or otherwise move relative to the superior and inferior members 112s, 112i. In another embodiment, the central members 118a, 118b, 118c, 118d can merely be disposed between the superior and inferior members 112s, 112i. The superior and inferior members 112s, 112i can optionally includes recesses formed therein and adapted to seat the central members 118a, 118b, 118c, 118d.

The shape and size of each central member 118a, 118b, 118c, 118d can also vary, but in one exemplary embodiment the central members 118a, 118b, 118c, 118d are adapted to allow movement between the superior and inferior members 112s, 112i. This can be achieved by, for example, forming the central members 118a, 118b, 118c, 118d, or at least a portion of the central members 118a, 118b, 118c, 118d, from a compressible or resilient material. Alternatively, the central members 118a, 118b, 118c, 118d can be inflatable to allow the superior and inferior members 112s, 112i to move relative to one another. In other exemplary embodiments, the central members 118a, 118b, 118c, 118d can have a shape that allows the superior and inferior members 112s, 112i to articulate relative thereto. While the shape can vary, in the illustrated exemplary embodiment the first and second central members 118a, 118b disposed between the arms 114s, 114i, 116s, 116i of the anterior portion 112b of the implant 100 each have a generally oblong shape, and the third and fourth central members 118c, 118d disposed between the superior and inferior members 112s, 112i of the posterior portion 112a of the implant 100 each have a generally spherical shape. A person skilled in the art will appreciate that a variety of other techniques can be used to movably couple the central members 118a, 118b, 118c, 118d to the superior and inferior members 112s, 112i, or to allow movement between the superior and inferior members 112s, 112i.

Figure 2C:
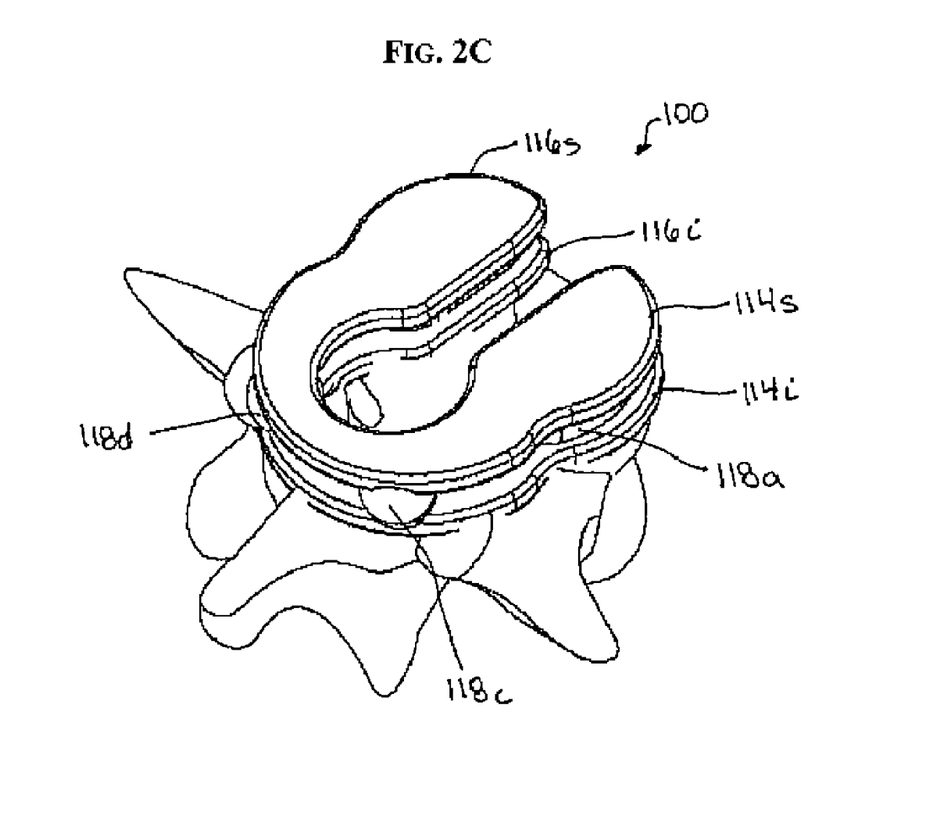
FIG. 2C is a superior perspective view of the spinal implant shown in FIG. 2A implanted between adjacent vertebrae, showing only the inferior vertebra.
Figure 2D:
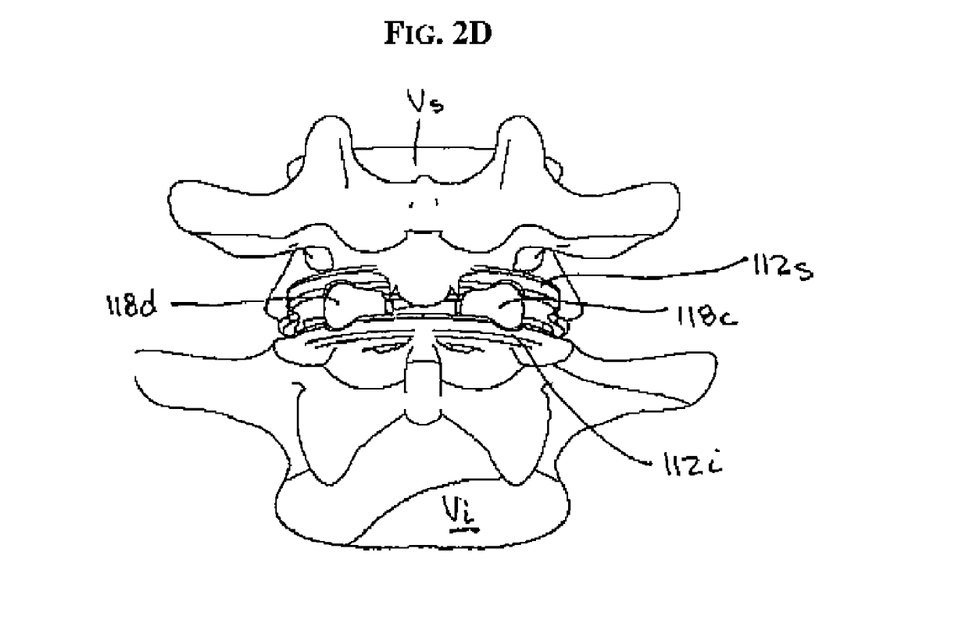
FIG. 2D is a posterior perspective view of the spinal implant shown in FIG. 2A implanted between adjacent superior and inferior vertebrae.

FIGS. 2C and 2D illustrate the implant 100 positioned between adjacent superior and inferior vertebrae $V_S$, $V_i$ (FIG. 2C only illustrates the inferior vertebra $V_i$). The implant 100 can be implanted using a variety of surgical techniques, and the particular technique can vary depending on the particular configuration of the implant 100. In one exemplary embodiment, a posterior surgical approach is used, as previously described with respect to FIGS. 1C-1D. Once the vertebrae $V_S$, $V_i$ are prepared, the implant 100 can be inserted between the adjacent vertebrae $V_S$, $V_i$ with the central members 118a, 118b, 118c, 118d pre-disposed between the superior and inferior members 112s, 112i. Where the central members 118a, 118b, 118c, 118d are inflatable, the implant 100 is preferably inserted between the adjacent vertebrae $V_S$, $V_i$ with the central members 118a, 118b, 118c, 118d in a deflated state. Once properly positioned between the adjacent vertebrae, an inflation medium, such as air or fluid, e.g., saline or gel, can be introduced into the central members 118a, 118b, 118c, 118d to inflate the central members 118a, 118b, 118c, 118d. The inflation medium can optionally be adapted to harden to form rigid central members 118a, 118b, 118c, 118d. While the central members 118a, 118b, 118c, 118d are preferably pre-disposed between the superior and inferior members 112s, 112i when the implant 100 is inserted between the adjacent vertebrae $V_s$, $V_i$, a person skilled in the art will appreciate that techniques could be used to allow the central members 118a, 118b, 118c, 118d to be implanted prior to implanting the superior and inferior members 112s, 112i.

While not shown, the implant 100 can also include features to facilitate engagement of the adjacent vertebrae at a location between the vertebrae and/or on the posterior surface of the adjacent vertebrae. As previously discussed, suitable techniques for mating the implant 100 to adjacent vertebrae include, by way of non-limiting example, surface features, such as teeth, that engage the endplates of the vertebrae and/or a posterior portion of the vertebrae, surface coatings or materials that allow bone growth into the implant 100 to occur, or other materials or features that will engage the adjacent vertebrae. By way of non-limiting example, in one exemplary embodiment the posterior portion 112a and/or the anterior portion 112b of the implant 100 can include teeth formed on the superior and inferior members 112s, 112i and adapted to engage the endplates of the adjacent vertebrae and/or a posterior portion of the vertebrae, such as the pedicles.

Figure 3A:
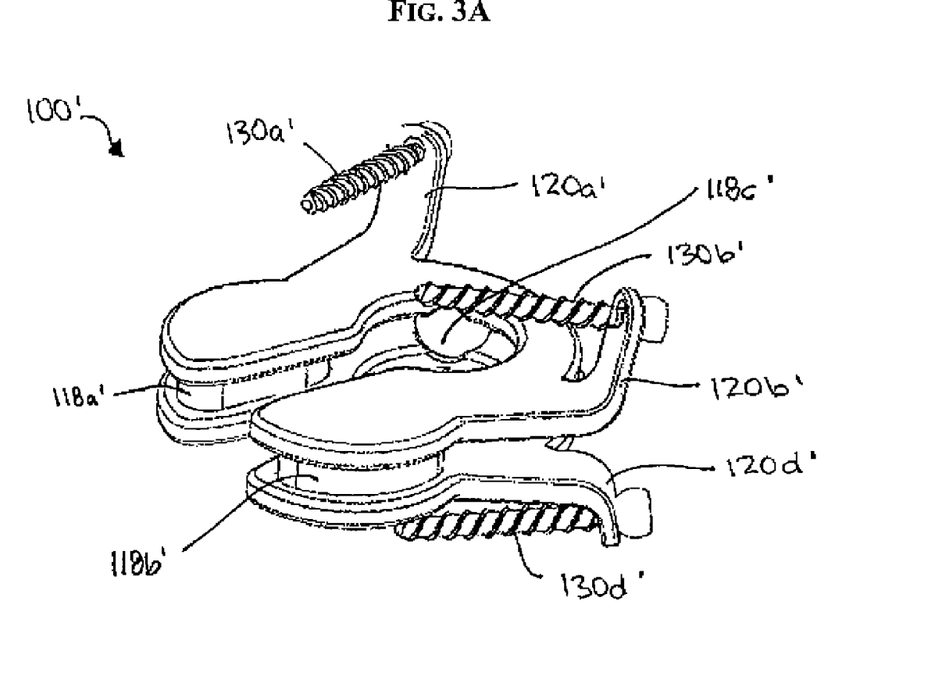
FIG. 3A is an anterior perspective view of yet another exemplary embodiment of a spinal implant having a multi-piece construction with extensions members formed thereon.
Figure 3B:
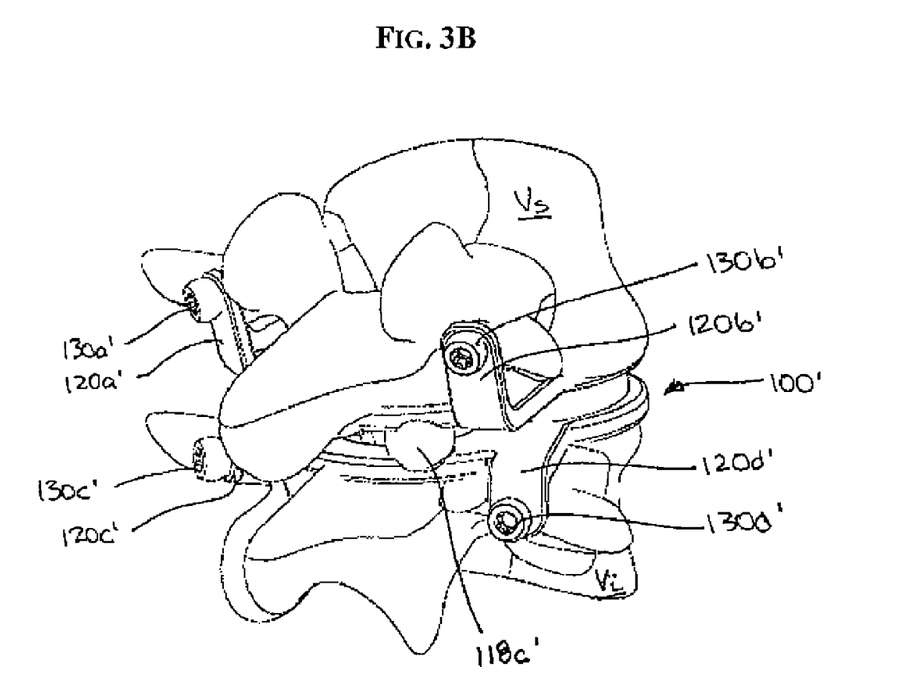
FIG. 3B is a posterior perspective view of the spinal implant shown in FIG. 3A implanted between and coupled to adjacent superior and inferior vertebrae.

In another exemplary embodiment, the implant 100 can include one or more extension members formed thereon or mated thereto and adapted to couple to at least one vertebrae. The extensions members can be similar to extension members 20a and 20b shown in FIGS. 1A-1D, or they can have a variety of other configurations that allow the implant 100 to couple to at least one adjacent vertebrae. By way of non-limiting example, FIGS. 3A and 3B illustrate one exemplary embodiment of an implant 100' that is similar to implant 100 but that has flange-like extension members 120a', 120b', 120c', 120d' formed thereon for mating the superior and inferior members 112s', 112i' to adjacent vertebrae. In particular, the implant 100' includes first and second extension members 120a', 120b' formed on the superior member 112s' and extending in a superior direction, and first and second extension members 120c', 120d' formed on the inferior member 112i' and extending in an inferior direction. The extension members 120a', 120b', 120c', 120d' can be formed at any location on the implant 100, but in an exemplary embodiment as shown the extension members 120a', 120b', 120c', 120d' are positioned on opposed lateral sides of the posterior portion 112a' of the implant 100' to allow the extension members 120a', 120b', 120c', 120d' to be coupled to the posterior surface of the adjacent superior and inferior vertebrae $V_S$, $V_i$, as shown in FIG. 3B.

Each extension member 120a', 120b', 120c', 120d' can have a variety of shapes and sizes. In the embodiment shown in FIGS. 3A and 3B, the extension members 120a', 120b', 120c', 120d' are integrally formed with the superior and inferior members 112s', 112i', and thus they have a substantially planar configuration. Each extension member 120a', 120b', 120c', 120d' also includes a thru-bore formed therein and adapted to receive a fastening element, such as a bone screw 130a', 130b', 130c', 130d', for mating the extension members 120a', 120b', 120c', 120d' to the vertebrae. A person skilled in the art will appreciate that a variety of other mating techniques can be used.

FIG. 3B illustrates the implant 100' in use, and as shown the first and second extension members 120a', 120b' are mated to a superior vertebra $V_S$, and the third and fourth extension members 120c', 120d' are mated to an adjacent inferior vertebrae $V_i$. As a result, the superior member 112s' is maintained in a substantially fixed position relative to the superior vertebra $V_S$, and the inferior member 112i' is maintained in a substantially fixed position relative to the inferior vertebra $V_i$. The central members 118a', 118b', 118', only three of which are shown in FIGS. 3A and 3B, allow the vertebrae $V_S$, $V_i$ to move relative to one another, thereby restoring normal function to the vertebrae $V_S$, $V_i$.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for stabilizing adjacent vertebrae, comprising:
    positioning a generally U-shaped posterior portion of an implant around a spinal cord and between resected facets of adjacent vertebrae, the posterior portion of the implant being adapted to couple to at least one of the adjacent vertebrae;
    positioning an anterior portion of the implant between the adjacent vertebrae such that the adjacent vertebrae are adapted to move relative to one another; and
    coupling the posterior portion of the implant to at least one of the adjacent vertebrae.

2. The method of claim 1, wherein the posterior portion of the implant is coupled to opposed lateral sides of at least one of the adjacent vertebrae.

3. A method for stabilizing adjacent vertebrae, comprising:
    accessing a patient's spinal column using a posterior surgical approach;
    removing a disc disposed between adjacent vertebrae; and
    posteriorly positioning a generally U-shaped posterior portion of an implant around a spinal cord and between facet joints of adjacent vertebrae, and positioning an anterior portion of the implant between the adjacent vertebrae, the U-shaped posterior portion being adapted to couple to at least one of the adjacent vertebrae.

4. The method of claim 3, further comprising coupling a posterior portion of the implant to at least one of the adjacent vertebrae.

5. The method of claim 3, wherein the posterior portion of the implant is coupled to at least one of the adjacent vertebrae by inserting at least one bone screw through at least one extension formed on the posterior portion of the implant and into bone.

* * * * *